(12) United States Patent
Kirkham (10) Patent No.: US 10,898,205 B2
(45) Date of Patent: Jan. 26, 2021

(54) SPIKED ELASTIC TOURNIQUET

(71) Applicant: Jeffrey B. Kirkham, Draper, UT (US)

(72) Inventor: Jeffrey B. Kirkham, Draper, UT (US)

(*) Notice: Subject to any disclaimer, the term of this patent is extended or adjusted under 35 U.S.C. 154(b) by 107 days.

(21) Appl. No.: 16/262,681

(22) Filed: Jan. 30, 2019

(65) Prior Publication Data
US 2019/0231363 A1    Aug. 1, 2019

Related U.S. Application Data

(60) Provisional application No. 62/624,461, filed on Jan. 31, 2018.

(51) Int. Cl.
*A61B 17/132* (2006.01)
*A61B 17/00* (2006.01)

(52) U.S. Cl.
CPC ...... *A61B 17/1322* (2013.01); *A61B 17/1327* (2013.01); *A61B 2017/00862* (2013.01)

(58) Field of Classification Search
CPC ........ A61B 17/132; A61B 2017/12004; A61B 17/1322; A61B 17/1327; A61B 2017/00862; A61B 17/135; A61F 5/32; A61H 9/0092; A41F 9/002; A41F 9/007; A41F 9/02; A41F 9/00; A41F 9/025; A41F 11/16; A41F 11/18; A44C 5/2066

USPC ............................................ 24/33 L; 40/633
See application file for complete search history.

(56) References Cited

U.S. PATENT DOCUMENTS

| 2014/0031861 A1* | 1/2014 | Teeslink | A61B 17/1325 |
| | | | 606/213 |
| 2017/0035440 A1* | 2/2017 | Hopman | A44B 11/223 |

FOREIGN PATENT DOCUMENTS

GB    2464989 A  *  5/2010  ......... A61B 17/1322

* cited by examiner

*Primary Examiner* — George J Ulsh
*Assistant Examiner* — Andrew P. Restaino
(74) *Attorney, Agent, or Firm* — Workman Nydegger (57) ABSTRACT

An improved type of tourniquet is disclosed herein. This tourniquet includes an elongated elastomeric body that includes first and second distal ends. The body is provided with a row of holes, where each hole is spaced a determined distance from one another. A first subset of at least three holes are located proximately to the first distal end and a second subset of at least three holes are located proximately to the second distal end. The tourniquet also includes a buckle that is affixed to or otherwise secured near the first distal end. Additionally, the tourniquet includes a set of one or more protruding spikes that are affixed to the elongated elastomeric body and that are positioned proximately to the buckle.

19 Claims, 7 Drawing Sheets

- 605 Wrap An Elongated Elastomeric Body Of A Tourniquet Around An Object At Least One Time, The Elongated Elastomeric Body Being Wrapped Around The Object In A First Wrapping Direction

- 610 Insert A Second Distal End Of The Elongated Elastomeric Body And At Least An Additional Portion Of The Elongated Elastomeric Body Through An Opening Of A Tri-Glide Buckle Affixed To A First Distal End Of The Elongated Elastomeric Body

- 615 Apply A Constrictive Tension Force On The Object Via The Tourniquet By Cinching The Additional Portion Of The Elongated Elastomeric Body

- 620 Wrap The Additional Portion Of The Elongated Elastomeric Body Around At Least A Part Of The Object And In A Second Wrapping Direction That Is Opposite To The First Wrapping Direction

- 625 Secure The Constrictive Tension Force On The Object By Inserting The First Spike Or The Second Spike Through A Hole Provided On The Additional Portion Of The Elongated Elastomeric Body

*Figure 6*

SPIKED ELASTIC TOURNIQUET

CROSS-REFERENCE TO RELATED APPLICATIONS

This application claims priority to U.S. Provisional Application Ser. No. 62/624,461, filed on Jan. 31, 2018 and entitled "SPIKED ELASTIC TOURNIQUET," the entirety of which is incorporated herein by reference.

BACKGROUND

A tourniquet is a type of constriction device used to occlude the flow of blood through a portion of a vascular system. Tourniquets can be used for humans and/or animals. Typically, tourniquets are used during periods of intense activity and/or stress (e.g., a combat situation or an accident). In some instances, injured persons might have to apply a tourniquet to their own bodies while they are still engaged in high stress situations. Accordingly, there is a need to provide a better type of tourniquet that can be used in any type of situation.

The subject matter claimed herein is not limited to embodiments that solve any disadvantages or that operate only in environments such as those described above. Rather, this background is provided to illustrate only one example technology area where some embodiments described herein may be practiced.

BRIEF SUMMARY

The disclosed embodiments relate to tourniquet apparatuses and methods for using said apparatuses.

In some embodiments, a tourniquet includes an elongated elastomeric body that includes first and second distal ends. This elongated elastomeric body is provided with a row of holes, where each hole is spaced a determined distance from one another. A first subset of at least three holes is located proximately to the first distal end and a second subset of at least three holes is located proximately to the second distal end. The tourniquet also includes a buckle that is affixed to or otherwise secured near/proximate to the first distal end. Additionally, the tourniquet includes a set of one or more protruding spikes that are affixed to the elongated elastomeric body and that are positioned proximately to the buckle.

In some embodiments, a tourniquet includes an elongated elastomeric body that includes a first and second distal end. This body also includes a row of holes, where each hole in the row is spaced a determined distance from one another. The tourniquet also includes a tri-glide buckle that is affixed to or otherwise secured near the first distal end. Additionally, the tourniquet includes a first spike and a second spike, both of which are affixed to the elongated elastomeric body and both of which are positioned proximately to the tri-glide buckle.

Some embodiments are directed to a method of using a tourniquet, where the tourniquet includes an elongated elastomeric body, a tri-glide buckle, and a first and second spike. The elongated elastomeric body includes a first distal end and a second distal end. It also includes a row of holes, where each hole in the row is spaced a determined distance from the other holes. The tri-glide buckle is affixed to or otherwise secured near the first distal end. The first and second spikes are also affixed to the elongated elastomeric body and are positioned proximately to the tri-glide buckle. This method includes wrapping the elongated elastomeric body around an object at least one time and in a first wrapping direction. After the elongated elastomeric body is wrapped around the object, the second distal end and at least an additional portion of the elongated elastomeric body is inserted through an opening of the tri-glide buckle. A constrictive tension force is applied on the object via the tourniquet by cinching the additional portion. Additionally, the additional portion is wrapped around at least a part of the object in a second wrapping direction opposite to the first wrapping direction. The constrictive tension force is then secured on the object by inserting the first spike or the second spike through a hole provided on the additional portion of the elongated elastomeric body.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Additional features and advantages will be set forth in the description which follows, and in part will be obvious from the description, or may be learned by the practice of the teachings herein. Features and advantages of the invention may be realized and obtained by means of the instruments and combinations particularly pointed out in the appended claims. Features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which.

DETAILED DESCRIPTION

The disclosed embodiments relate to tourniquets and to methods of using said tourniquet.

In some embodiments, a tourniquet includes an elongated elastomeric body (or simply "body"), a buckle, and a set of one or more protruding spikes. The body includes first and second distal ends and a number of holes that are spaced apart from one another. Some of the holes are positioned proximately to the first distal end and some are positioned proximately to the second distal end. The buckle is affixed to the body near the first distal end. The spikes are also affixed to the body and are positioned proximately to the buckle.

In some embodiments, a tourniquet includes a body, a tri-glide buckle, and first and second spikes. The body includes first and second distal ends and a number of spaced-apart holes. The tri-glide buckle is affixed to the body near the first distal end. The spikes are also affixed to the body and are positioned proximately to the tri-glide buckle.

Some embodiments are directed to a method of using a tourniquet. The tourniquet's body is wrapped around an object at least one time in a first wrapping direction. After the body is wrapped around the object, the body's second distal end and an additional length or portion of the body is inserted into the tourniquet's tri-glide buckle. A constrictive force is then applied on the object by cinching the additional portion of the body. The additional portion of the body is also wrapped around at least a part of the object in a second wrapping direction opposite to the first wrapping direction. The constrictive tension force is then secured by inserting the tourniquet's spike through a hole provided on the additional portion of the body.

Improved Tourniquet Design

Figure 1:
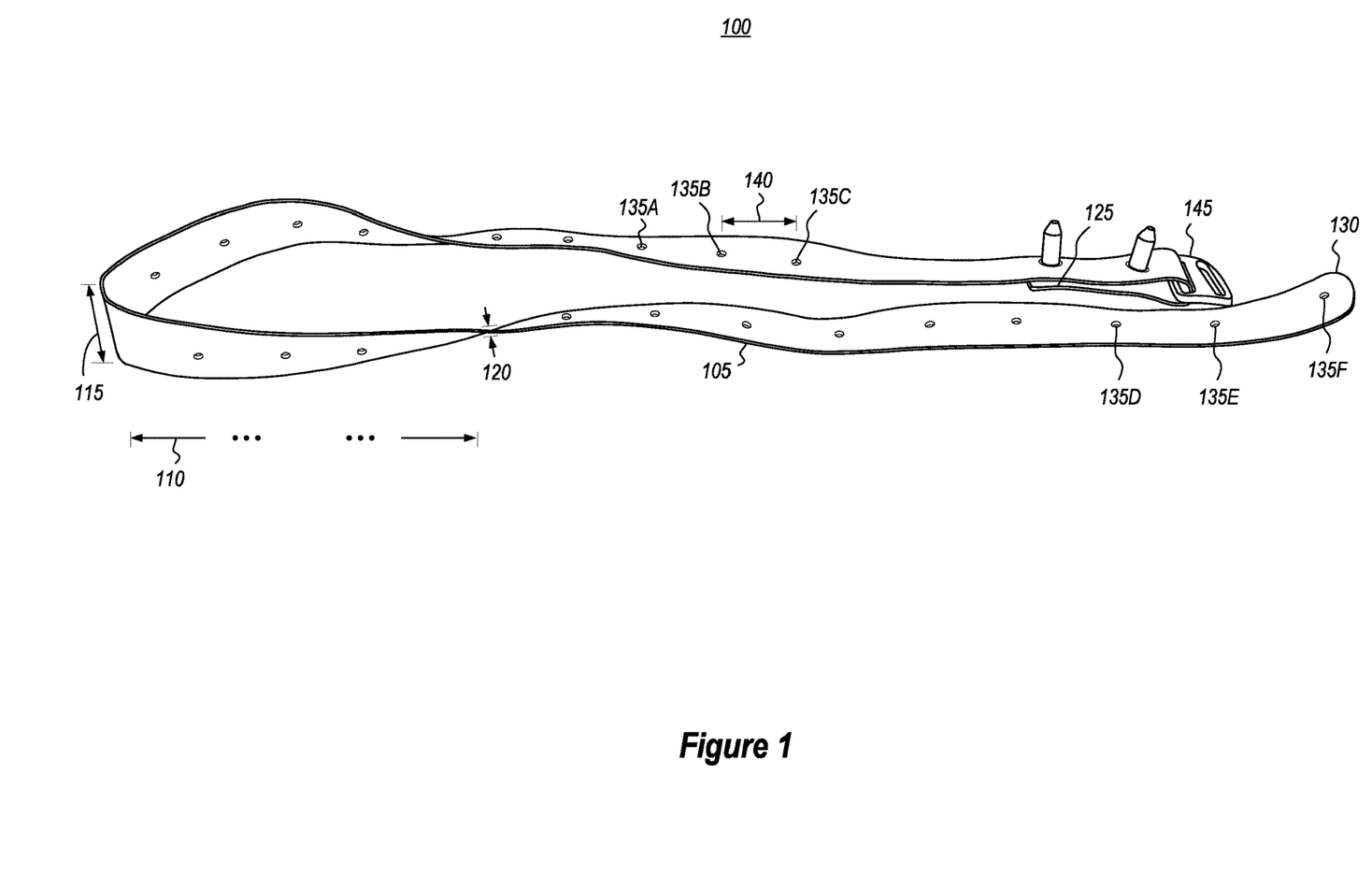
FIG. 1 illustrates an example tourniquet that can be used to occlude the flow of blood through a vascular system.

Attention will now be directed to FIG. 1 which depicts an illustration of one example implementation of a tourniquet 100. Tourniquet 100 includes an elongated elastomeric body (or simply "body") 105.

Body 105 may be formed of any kind or type of rubber-like polymer that is capable of reforming and/or retaining its original shape after or while being stretched or manipulated in some manner. As examples only, the rubber-like polymers of body 105 include, but are not limited to, any kind of synthetic rubber, polyurea, thermoplastic elastomers, any kind of polyethylene, silicone, latex, and any kind of rubber. Accordingly, body 105 may be formed of any kind of material that is suitable for bearing a load and that can reform or retain to its original shape after the load is removed or while the load is being applied.

As indicated earlier, tourniquets are used to occlude or restrict the flow of blood through a vascular system. In many instances, a tourniquet (e.g., tourniquet 100) will be wrapped around a person's extremity/appendage (e.g., an arm or a leg) or an animal's appendage. Tourniquet 100 can also be wrapped around any other type of object so as to restrict the flow of liquid through that object. As an example, tourniquet 100 can be wrapped around a flexible pipe so as to restrict the flow of liquid through that pipe. Accordingly, tourniquet may be wrapped around any type of object so as to restrict the flow of material through that object. While the remaining portion of this disclosure focuses on wrapping tourniquet 100 around an appendage, it will be appreciated that the disclosed embodiments may be used in a variety of situations and are not limited simply to appendage-type applications.

Accordingly, it will be appreciated that body 105 can be designed so as to be sufficiently long such that body 105 can be wrapped around any type of appendage or other object and can be wrapped around those objects as many times as desired. For example, body 105 will be long enough to wrap around an appendage at least once, but it may also be wrapped around the appendage multiple times (e.g., 2, 3, 4, 5, or more times around the appendage).

Body 105 is shown as having a length 110, a width 115, and a thickness 120. Length 110 is shown as being significantly longer than either width 115 or thickness 120. It will be appreciated that body 105 may be any length, width, or thickness.

Length 110 is typically in the range of anywhere between and including 1 foot up to and including 6 feet, though larger or smaller lengths may be used as well. For instance, length 110 may be less than 1 foot; 1 foot; 1.25; 1.5; 1.75; 2; 2.5; 3; 4; 5; 6; or more than six feet in length. Accordingly, body 105 may be any length, and it is not restricted solely to lengths spanning between 1 foot and 6 feet.

Width 115 is typically in the range of anywhere between and including 0.05 inches up to and including 3 inches, though larger or smaller widths may be used as well. For instance, width 115 may be 0.05; 0.06; 0.07; 0.08; 0.09; 0.1; 0.5, 1.0; 2.0; or 3.0 inches. These widths provide adequate structural strength so that tourniquet 100 can bear a load without ripping or otherwise failing to apply a constrictive tension force on an object.

Thickness 120 is typically in the range of anywhere between and including 0.05 inches up to and including 0.25 inches, though larger or smaller thicknesses may be used as well. Thickness 120 is also designed to be sufficiently thick so that tourniquet 100 can properly bear a load without ripping or otherwise failing to apply a constrictive tension force on an object. In cases where tourniquet 100 is used on an appendage, then thickness 120 is designed to be sufficiently thick so as to bear a load suitable for occluding the flow of blood in a vascular system.

Body 105 is shown as being generally planar in shape. For example, in some implementations, body 105 has a rectangular prism shape. It will be appreciated, however, that the edges of body 105 may be substantially right-angle edges or, alternatively, those edges may be rounded to any degree or in any manner.

Body 105 also includes a first distal end 125 and a second distal end 130. In some embodiments, first distal end 125 and/or second distal end 130 are rounded to form a semi-circular end. In other embodiments, first distal end 125 and/or second distal end 130 include cornered edges, where the cornered edges may approximate a 90-degree angle or, alternatively, may have somewhat rounded cornered edges.

Width 115 and thickness 120 are designed so as to securely support any number of holes along body 105. FIG. 1 illustrates some of these holes, such as holes 135A, 135B, 135C, 135D, 135E, and 135F. Although only six holes are labeled, body 105 may support any number of holes.

The holes (e.g., 135A, 135B, 135C, 135D, 135E, and 135F) constitute a row of holes that are formed along a central elongated path or region of body 105. It will be appreciated that body 105 may include any number of holes, but in most situations, body 105 includes at least six holes.

Furthermore, as generally shown in FIG. 1, each hole may be positioned a determined distance 140 from any other hole. This determined distance 140 may be any distance, but typical distances range between and including 0.75 inches and 4 inches, though larger or smaller distances may be used. In some embodiments, therefore, each hole is typically no closer in distance to another hole than 0.75 inches and no further in distance than 4 inches. In some embodiments, the determined distance is 1 inch. In some embodiments, the distances between holes varies between the range. As an example, two holes may be 0.75 inches apart while two other holes may be 1 inch apart. Accordingly, any distance may be provided between the holes.

In some implementations, a first set of at least three holes (e.g., holes 135A, 135B, and 135C) are located near or proximate to the first distal end 125, and a second set of at least three different holes (e.g., holes 135D, 135E, and 135F) are located near or proximate to the second distal end 130. That is, in some embodiments, a subset of holes is provided near the first distal end 125 and a different subset of holes is provided near the second distal end 130. For example, body 105's middle portion (in the length dimension) may be structured so as to not include any holes such that there is a portion of length 110 that is without any holes, or is "hole-less".

By way of an additional example, in some embodiments, body 105 is provided with a first set of holes located near the first distance end 125. Then, body 105 has a length of space/area that does not include a set of holes. Following this length, another row of holes may be formed in body 105. Following that row of holes, body 105 may have another length of space/area that does not include a set of holes, and so on and so forth until a set of holes are provided near the second distal end 130. In these implementations, therefore, body 105 is provided with multiple discrete rows of holes that are separated from one another by areas where there are no holes.

As another example, body 105 may include three holes located near the first distal end 125, where the three holes are separate by a distance between 0.75 inches and 4 inches. After the last of the three holes, there may be a length of anywhere between 3 to 9 inches where there are no holes in body 105. After this 3 to 9-inch length, body 105 may again include another set of three holes separate by a distance between 0.75 inches and 4 inches. Following the last hole in that set, there may be another length of anywhere between 3 to 9 inches where there are no holes in body 105. This pattern may extend until the second distal end 130 is reached. Of course, other numbers may be used instead of the numbers recited above.

In some embodiments, body 105 includes a continuous row of holes that starts at or near the first distal end 125 and that ends at or near the second distal end 130, where those holes are separated by a distance ranging between 0.75 inches and 4 inches. In such scenarios, therefore, holes are provided or spaced along the entire length 110 of body 105 without large areas that are absent of holes (i.e. hole-less portions). Accordingly, in some implementations, a row of holes extends along a majority of a length of the elongated elastomeric body (e.g., as in the case of a continuous row of holes). In some implementations, the row of holes extends along a minority of a length of the elongated elastomeric body (e.g., as in the case where a first set of holes is provided near the first distal end 125 and a second set of holes is provided near the second distal end 130 and there are no or few holes provided in between those two sets).

As another example, suppose a subset of holes includes 3 holes. Within this subset, each hole may be spaced 0.75; 1.0; 1.25; 1.5; 1.75; 2.0; 3.0, or 4.0 inches from each other. In another example, a subset of holes may include 4 holes, where the holes are spaced 1 inch from each other. In another example, a subset of holes may include 5 holes, where the holes are spaced 1 inch from each other. In yet another example, a subset of holes may include 6 holes, where the holes are spaced 1 inch from each other. Accordingly, it will be appreciated that a subset of holes may include any number of holes, and these holes may be spaced any determined distance 140 from one another.

FIG. 1 also shows that a buckle 145 (e.g., a tri-glide buckle, tri-glide slide, slide, or any other type of buckle) is affixed to or otherwise secured near the first distal end 125 of body 105. Buckle 145 may be formed of any material. Example materials include, but are not limited to, any kind of plastic and any kind of metal.

Figure 2A:
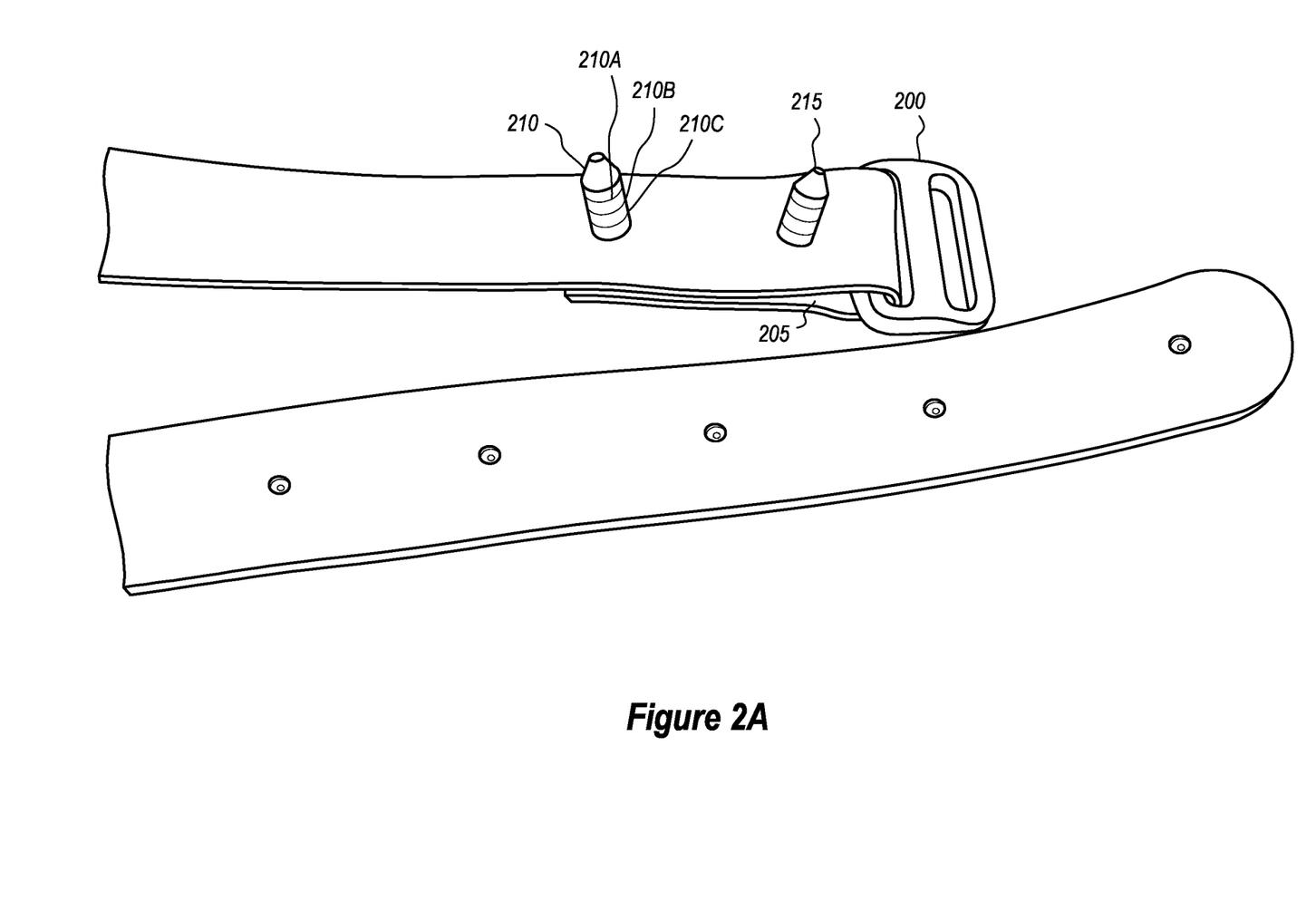
FIG. 2A shows a close-up view of a spiked portion of the example tourniquet and of the buckle portion of the example tourniquet.

Turning briefly to FIG. 2A, this figure shows a close-up view of a tri-glide buckle 200, which is an example implementation of buckle 145 from FIG. 1. Tri-glide buckle 200 provides a 2:1 mechanical advantage when the tourniquet bears a load.

By way of background, a 2:1 mechanical advantage means that the force used when pulling with the tri-glide buckle 200 is approximately half the force of the weight of the load (or the applied constrictive tension force). Tri-glide buckle 200 provides significant benefits to a user because that user is not required to exert as much force or energy when operating the tourniquet, particularly as compared to many of the other tourniquets in the industry.

As indicated earlier, tourniquets are often used during high stress situations. By including tri-glide buckle 200, which is capable of providing a 2:1 mechanical advantage, a person using the tourniquet will not have to exert nearly as much effort as when a tourniquet that does not include tri-glide buckle 200 is used.

Although the figures show a tri-glide buckle 200, it will be appreciated that any type of mechanism capable of providing at least a 2:1 mechanical advantage may be used. Examples include pulleys, metallic rings, metallic squares (e.g., similar to a tri-glide buckle but without the middle track portion), and so forth. Accordingly, the disclosed embodiments are not limited solely to tri-glide buckles. Furthermore, while the remaining portion of this disclosure focuses on the use of a tri-glide buckle, it will be appreciated that any of the above-mentioned mechanisms may alternatively be used.

Returning to FIG. 1, buckle 145 may be affixed to or securely attached to tourniquet 100 near or proximate to the first distal end 125. For example, buckle 145 is currently shown as being secured in place by inserting the first distal end 125 through an opening of buckle 145. A portion of body 105 was then pulled through that opening. The first distal end 125 was then secured in place in a manner so that the first distal end 125 will not escape back through the opening of buckle 145. That is, in some implementations, buckle 145 may be securely positioned on body 105 by wrapping a portion of body 105 through one of the openings of buckle 145 and then securing that portion so that body 105 will not be dislodged from buckle 145.

In the embodiment shown in FIG. 2A, a portion 205 of the body is passing through one of the openings of the tri-glide buckle 200. This portion 205 is then secured through the use of a set of one or more spikes (e.g., spikes 210 and 215) that pass through one or more of the holes that are positioned near the distal end of the body. As such, spikes 210 and 215 can be used to secure the portion 205 from falling out or otherwise coming loose from tri-glide buckle 200. In this regard, at least one spike (e.g., 210 or 215) in a set of one or more protruding spikes secures the elongated elastomeric body to a buckle (e.g., tri-glide buckle 200) such that the elongated elastomeric body is fixedly attached to the buckle via the at least one spike.

FIG. 2A also shows that spikes 210 and/or 215 may, in some embodiments, include one or more ribs or ribbed portions (e.g., rib 210A, 210B, 210C). More detail on these ribs will be provided later.

Returning to FIG. 1, body 105 may be secured to buckle 145 in other ways as well. As an example, body 105 may be glued or cemented to buckle 145, it may be stapled to buckle 145, or it may be melded to buckle 145. Regardless of which process is used, buckle 145 is securely affixed to body 105.

Figure 3:
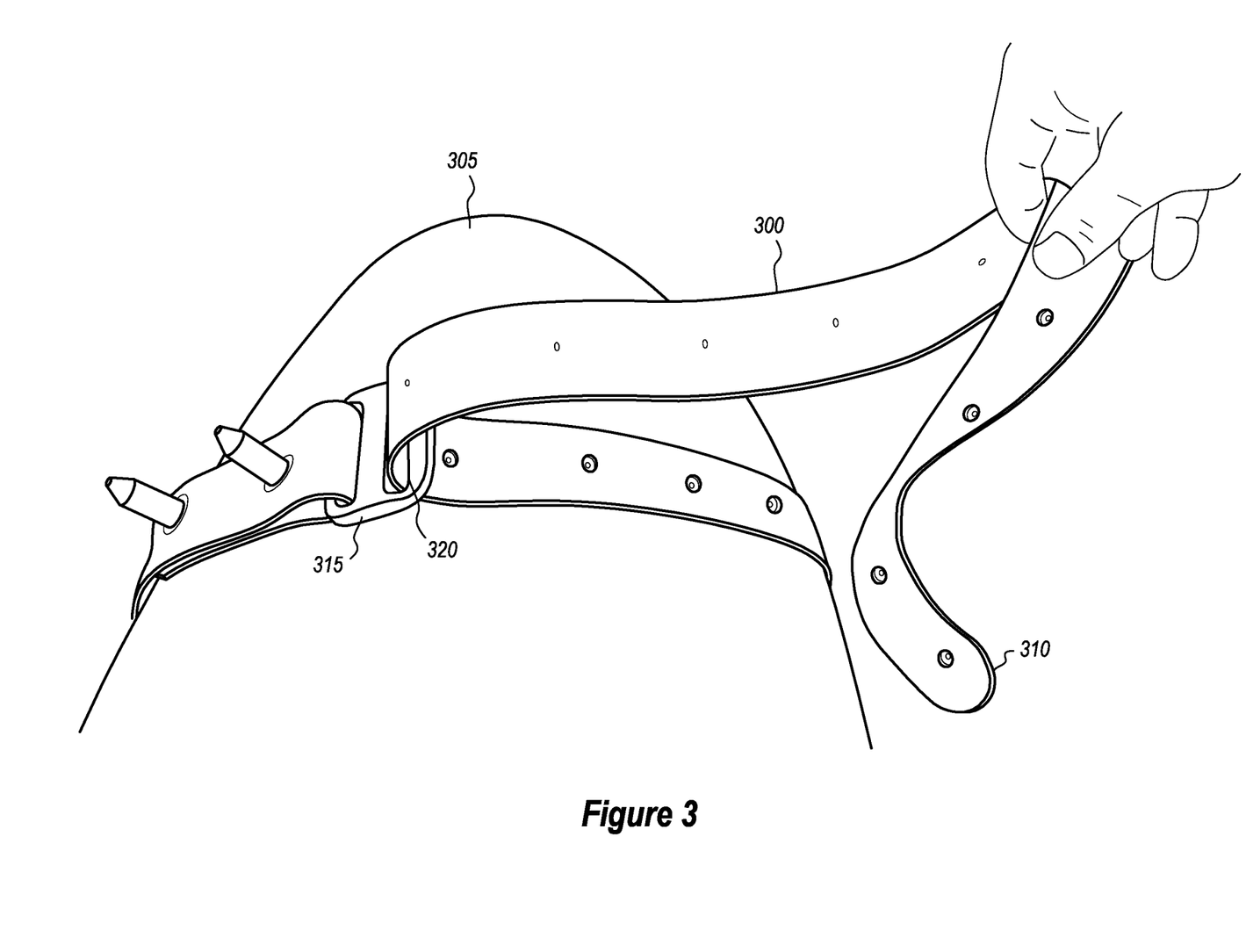
FIG. 3 shows a close-up view of a tri-glide buckle portion of the example tourniquet, which tri-glide buckle is used to provide a 2:1 mechanical advantage.

FIG. 3 shows a tourniquet 300 that is an example implementation of tourniquet 100 from FIG. 1. When used, tourniquet 300 is wrapped around an appendage 305 (or another object) at least once (but perhaps more than once).

FIG. 3 shows that tourniquet 300 has been wrapped around appendage 305 (i.e. a thigh) only one time. By wrapping tourniquet 300 around appendage 305, tourniquet 300 can be used to cut off, restrict, or otherwise occlude the flow of blood that is being transported to or through appendage 305. Once tourniquet 300 is wrapped at least once around appendage 305, then the distal end 310 that does not have a buckle 315 may be inserted into one of the openings 320 of the buckle 315. Once inserted, then tourniquet 300 can be cinched so as to apply a constructive tension force on appendage 305 and restrict the flow of blood therethrough.

Figure 4:
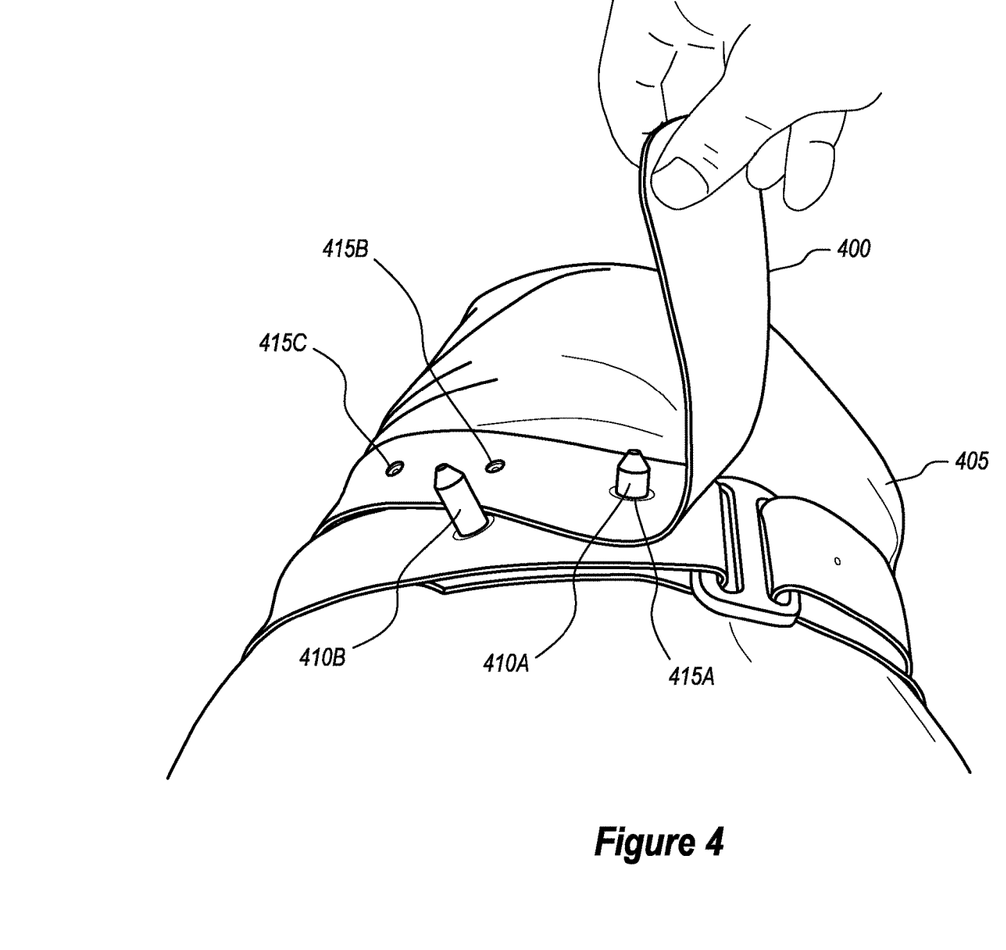
FIG. 4 illustrates a close-up view of how the spikes may be used to secure the fastening of the tourniquet in order to occlude the flow of blood.

FIG. 4 shows another example tourniquet 400 that is representative of the tourniquets discussed in the earlier figures. To secure tourniquet 400 in place after being wrapped around appendage 405 (i.e. to persist the pressure applied by tourniquet 400), a spike (e.g., spike 410A or 410B) may be inserted into one or more of the holes (e.g., holes 415A, 415B, or 415C). Holes 415A, 415B, and 415C are representative of holes 135A-135F in FIG. 1. In this manner, tourniquet 400 will continuously exert pressure against appendage 405 because the pressure is persisted as a result of the cinching pressure of tourniquet 400 being secured via the one or more spikes 410A or 410B.

The disclosed embodiments may include any number of spikes. For example, the embodiments may include as few as one spike while in other cases some embodiments may not have an upper limit on the number of spikes. Typically, however, the embodiments include anywhere between 1 and 3 spikes. In the example tourniquets shown in FIGS. 1 through 4, those tourniquets included two spikes.

The spikes may be structured in different ways. In some embodiments, as shown in FIG. 2A, a spike 210 may have one or more ribbed portions (e.g., rib 210A, rib 210B, and rib 210C) that extend up a height of spike 210. These ribs (or ribbed portions) 210A-210C are useful when spike 210 is inserted into one of the holes. Accordingly, each spike in a set of one or more protruding spikes includes one or more ribbed portions. In some implementations, different spikes include different numbers of ribbed portions. The ribs can be used to prevent any slippage of the holes off of the spikes.

Figure 2B:
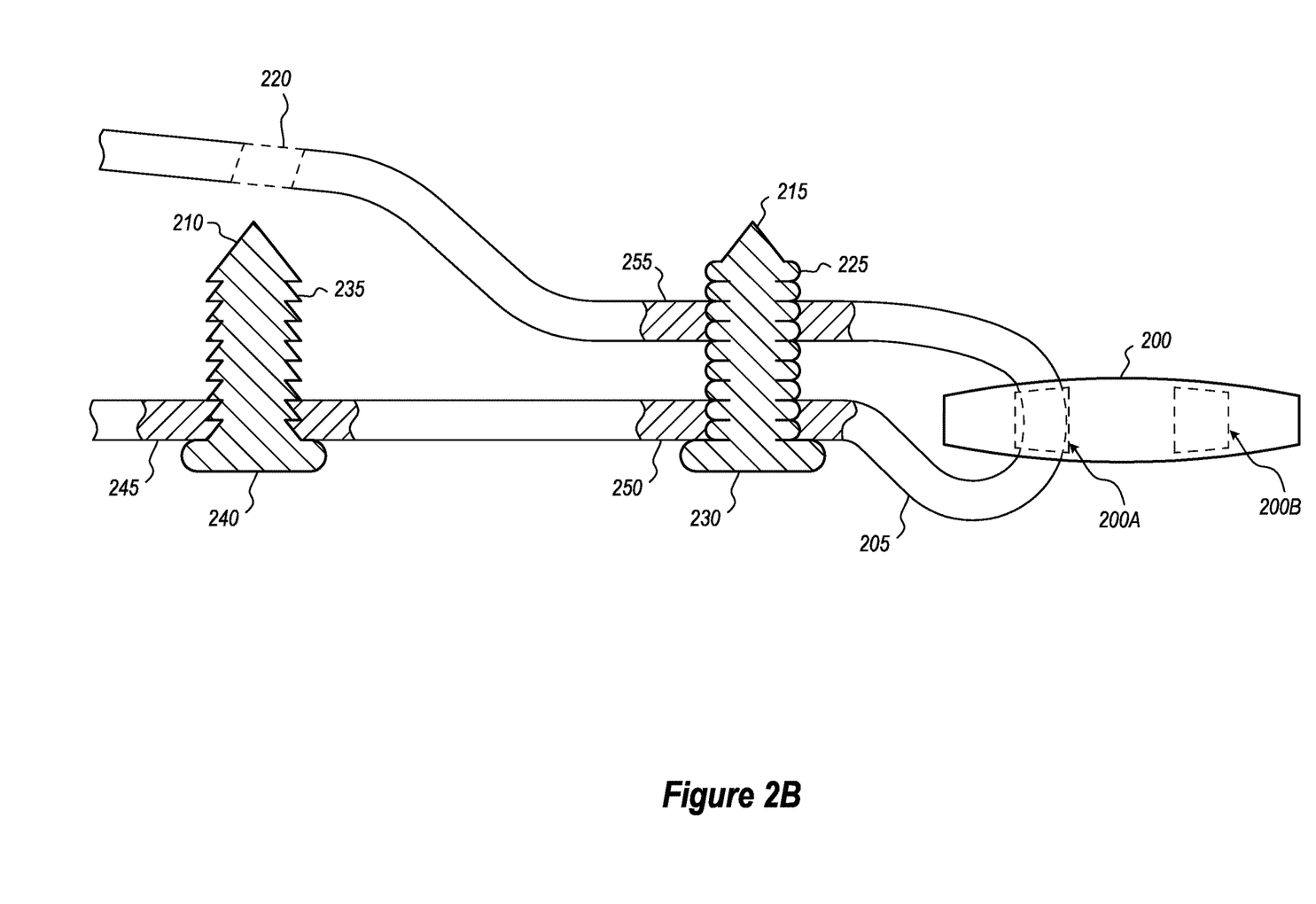
FIG. 2B shows another close-up view of the spiked portion of the tourniquet and how those spikes can be affixed to the body of the tourniquet.

FIG. 2B shows another depiction of the tourniquet's spikes and buckle portions. The diagonal line sections (e.g., section 245, section 250, and section 255 along with the diagonal line section of the spikes 210 and 215) a representative of a cross-sectional side perspective view while the non-diagonal line sections are not cross-sectional views. In other words, the portions having diagonal lines are portions that were cut in half and then viewed from a side perspective. Specifically, FIG. 2B shows the tri-glide buckle 200 with a first opening 200A and a second opening 200B through which different portions of the body are able to pass through. As an example, FIG. 2B shows portion 205 of the body passing through opening 200A of the tri-glide buckle 200. FIG. 2B also shows spikes 210 and 215 and a hole 220 (which is representative of any of the holes discussed thus far) through which any spike (e.g., spike 210) can pass through.

FIG. 2B also shows, in a partial cutaway, some different structural configurations for the ribbed portions that were discussed earlier. That is, the spikes 210 and 215 may include different texturing or surfacing in order to ensure that when spikes 210 and 215 are fixed within holes of the tourniquet, then the spikes 210 and 215 will not slip loose or otherwise become inadvertently dislodged. Spike 215 is shown as including knurls 225 and a base 230. Knurls 225 are just one example implementation of the ribs or texturing that were discussed earlier. When spike 215 is pushed into one of the tourniquet's holes, then knurls 225 will prevent spike 215 from becoming dislodged. The base 230 is provided as a mechanism to ensure that spike 215 is not pushed entirely through one of the holes. That is, base 230 operates as a bottom support mechanism to ensure that spike 215 is secured to the tourniquet. Base 230 also operates to ensure that spike 215 remains affixed to the tourniquet's body.

Spike 210 includes a different type of texturing in the form of tapering 235 (e.g., a type of barbed tapering). Similar to spike 215, spike 210 also includes a base 240 used to secure spike 210 to the tourniquet and used to ensure that spike 210 will not fully push through a hole (e.g., hole 220). Accordingly, spikes 210 and 215 can be used to secure the body to the tri-glide buckle 200. They are also used to secure a constrictive tension force when the tourniquet is applied to some object, as will be described in more detail later.

Figure 5:
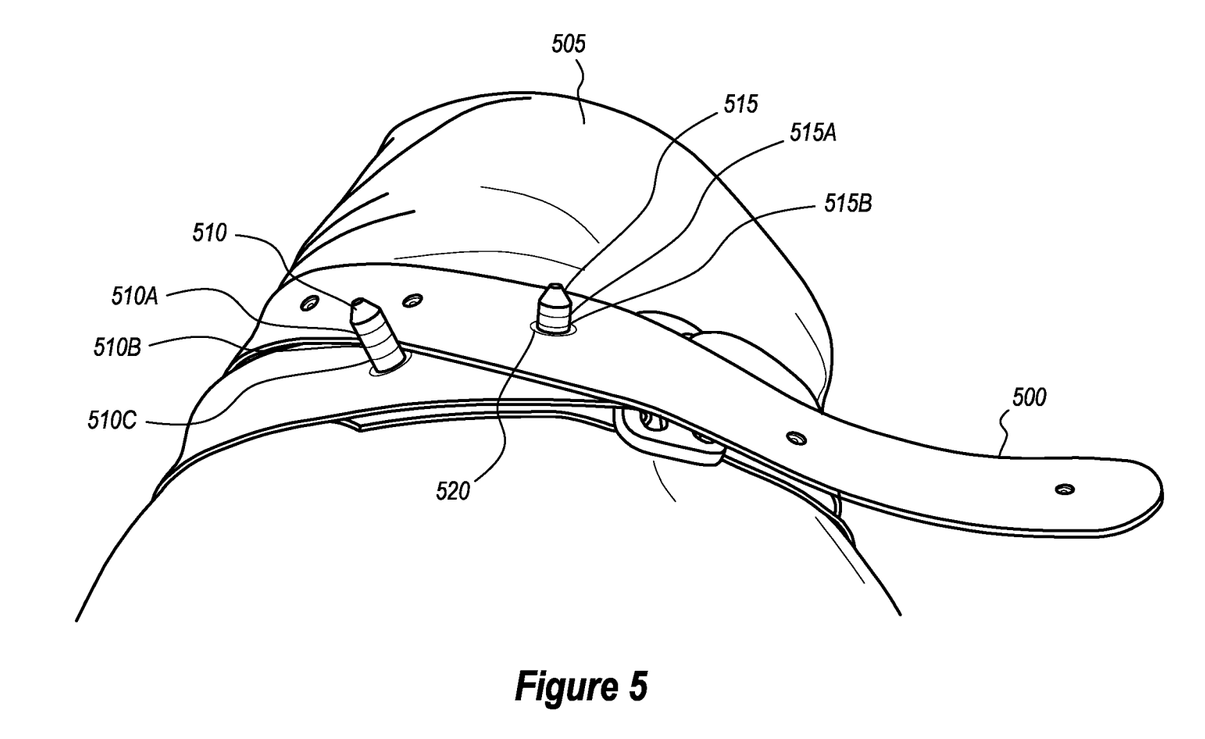
FIG. 5 shows another close-up view of how the spikes are used to secure the tourniquet in place.

FIG. 5 shows a tourniquet 500, which is representative of the earlier tourniquets discussed thus far. Tourniquet 500 is wrapped around appendage 505. Furthermore, tourniquet 500 includes a first spike 510, which includes rib 510A, rib 510B, and rib 510C. Tourniquet 500 also includes a second spike 515, which includes rib 515A and rib 515B.

As shown, spike 515 has been inserted into a hole 520 of tourniquet 500 to secure tourniquet 500 in place around appendage 505. Ribs 515A and 515B are beneficially provided to help further secure tourniquet 500 in place so as to prevent hole 520 from inadvertently slipping off of spike 515. That is, by including the ribs 510A-C and ribs 515A-B, tourniquet 500 is less likely to slip off of its spikes because tourniquet 500 will catch, or be restrictively caught, on each of the ribs.

Worthwhile to note, the embodiments may include any number of ribs (i.e. ribbed portions). For example, the number of ribbed portions may be one, two, three, four, five, six, seven, eight, nine, ten, one hundred, or any number therebetween. Some embodiments, however, do not include a ribbed portion. Instead, the spikes may simply have a flat outer surface.

In some embodiments, a spike may include a tapered top (i.e. a spike-like shape). This spike-like shape is useful for when the spike is inserted into one of the holes because it helps guide the spike through the hole. Some embodiments, however, do not include a tapered top. Instead, some embodiments simply include a flat top or even a semi-circular top. In some embodiments, the spike is flared at its end (rather than being tapered, pointed, flat, or circular). By flaring, it is meant that a portion of the tip may be larger than the spike's main length portion. This flaring can help retain or secure the body in place when positioned over the spike so that the body does not slip off. Slippage can be eliminated or reduced, therefore, as a result of the larger tip portion of a spike. In some embodiments, the spike end is shaped like a spade, cone, flange, or any other tapered or flared shape. The shape can also be symmetric or asymmetric, relative to the central axis of the spike. Finally, it will also be noted that the spike can be cylindrical or, alternatively, flattened or not perfectly cylindrical and symmetric about the central axis (which extends along the main length of the spike).

The spikes (e.g., spikes 510 and 515 in FIG. 5) may also be of any length and any diameter. Typical lengths range from 0.25 inches up to 1.5 inches. The length is structured so that the spike is able to adequately support the body of the tourniquet when the spike is inserted into a hole in the body. In some cases, a tourniquet may have multiple spikes, where each of those spikes is of a different length and/or diameter from one another. In some cases, one or more spikes share similar dimensions while one or more other spikes have different dimensions.

In some embodiments, the diameter of the spike is a determined amount larger than the diameter of the holes. As a result, a hole is somewhat stretched when the spike is inserted therein. Such stretching also helps secure the body to the spike. Accordingly, in at least some embodiments, each spike in the set of one or more protruding spikes has a width or diameter that is a determined amount larger than a width of the holes in the row of holes. In some embodiments, the diameter is substantially the same as the diameter of the holes in the tourniquet.

Accordingly, in some embodiments, a tourniquet (e.g., tourniquet 100 from FIG. 1) includes an elongated elastomeric body (e.g., body 105) that includes a first distal end (e.g., first distal end 125) and a second distal end (e.g., second distal end 130). The elongated elastomeric body is provided with a row of holes (e.g., holes 135A-F in FIG. 1), where each hole in the row is spaced a determined distance (e.g., determined distance 140) from one another. Additionally, a first subset of at least three holes (e.g., holes 135A, 135B, and 135C) are proximate to the first distal end, and a second subset of at least three holes (e.g., holes 135D, 135E, and 135F) are proximate to the second distal end. The tourniquet also includes a buckle (e.g., buckle 145 from FIG. 1) that is affixed to or at least positioned near to the first distal end of the elongated elastomeric body. Additionally, the tourniquet includes a set of one or protruding spikes (e.g., spikes 410A and 410B from FIG. 4) that are affixed to the elongated elastomeric body and that are proximate to the buckle. In some embodiments, the buckle is a tri-glide buckle. Additionally, in some embodiments, the set of one or more protruding spikes includes a first spike and a second spike.

Example Method(s) of Use

The following discussion now refers to a number of methods and method acts that may be performed. Although the method acts may be discussed in a certain order or illustrated in a flow chart as occurring in a particular order, no particular ordering is required unless specifically stated, or required because an act is dependent on another act being completed prior to the act being performed.

Figure 6:
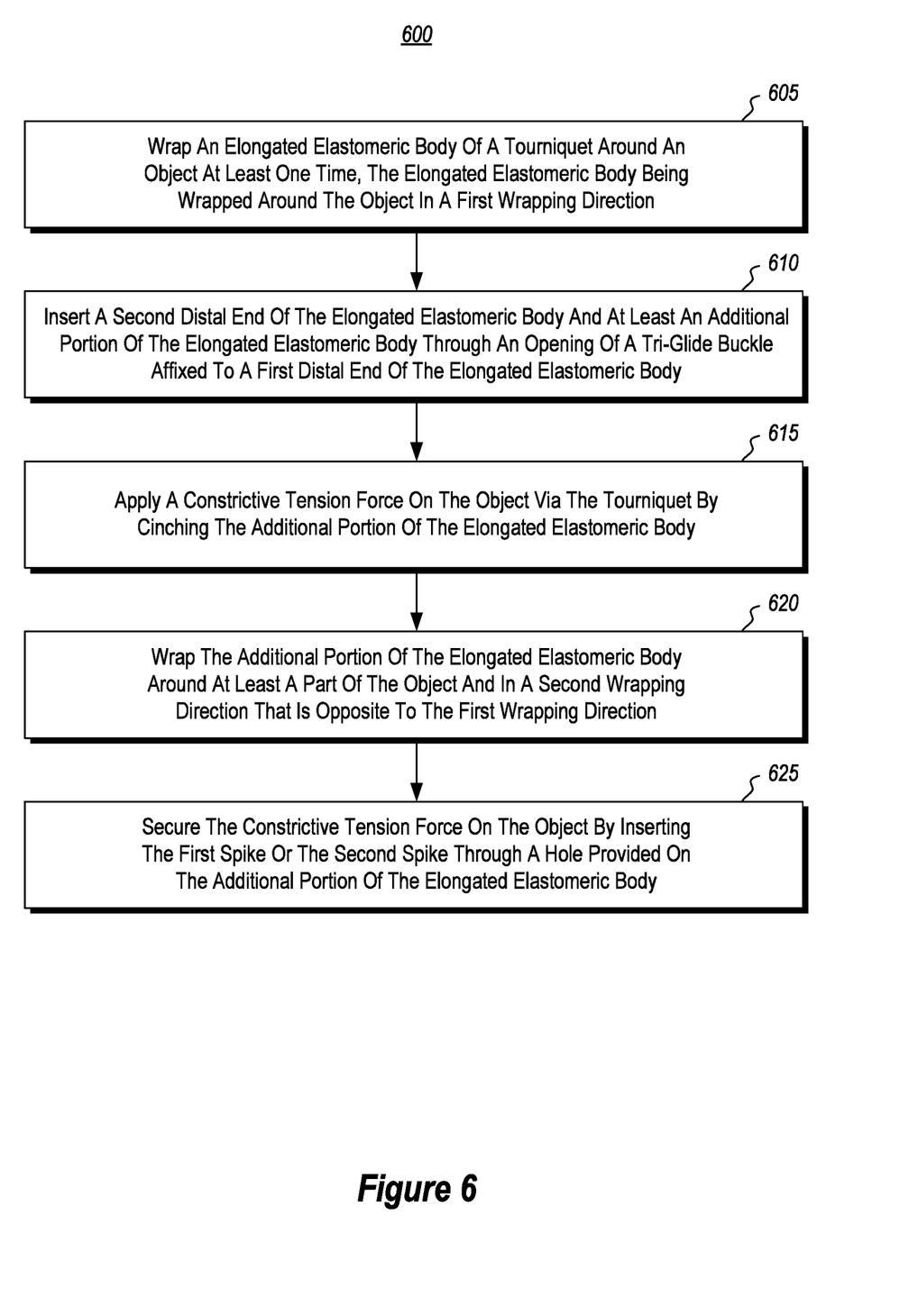
FIG. 6 illustrates a flowchart of an example method for using the improved tourniquet.

FIG. 6 illustrates a flowchart of an example method 600 for operating a tourniquet. This tourniquet may be in the form of the tourniquets that were discussed earlier. For instance, the tourniquet may include (i) an elongated elastomeric body that includes a first distal end and a second distal end and that is provided with a row of holes, each hole in the row being spaced a determined distance from one another; (ii) a tri-glide buckle that is affixed to the body at a position near the first distal end; and (iii) a first spike and a second spike that are both affixed to the elongated elastomeric body and that are positioned proximately to the tri-glide buckle.

Method 600 includes an act 605 of wrapping at least a portion of the elongated elastomeric body around an object (e.g., an appendage) at least one time, though it may be wrapped around more than once. Furthermore, at least the portion of the elongated elastomeric body is wrapped around the object in a first wrapping direction. As an example, FIG. 3 shows how tourniquet 300 is wrapped around the appendage 305 in a first wrapping direction. For example, from the buckle 315, the tourniquet 300 is wrapped counterclockwise around appendage 305. This counterclockwise direction can be considered as the first wrapping direction.

After at least the portion of the elongated elastomeric body is wrapped around the object, act 610 includes inserting the second distal end and at least an additional portion of the elongated elastomeric body through an opening of the tri-glide buckle. FIG. 3 also shows how distal end 310 (i.e. the so-called second distal end) can be inserted through an opening (e.g., opening 320) of buckle 315. Furthermore, a length of the tourniquet 300 can be pulled through the opening 320, as shown in FIG. 3.

Act 615 includes applying a constrictive tension force on the object via the tourniquet by cinching the additional portion of the elongated elastomeric body. FIG. 3 also shows how the tourniquet 300 can be tightened around the appendage 305 so as to apply a constrictive tension force on the appendage 305.

Act 620 includes wrapping the additional portion of the elongated elastomeric body around at least a part of the object and in a second wrapping direction that is opposite to the first wrapping direction. FIG. 3 shows how the distal end 310 is being wrapped around the appendage 305 in a clockwise direction such that it is being wrapped in a direction opposite to the initial wrapping direction. In doing so, the tourniquet 300 can be progressively cinched and tightened about the appendage 305. FIG. 4 also shows how the tourniquet is wrapped in the clockwise direction. It will be appreciated that the additional portion can be wrapped around the appendage any number of times so as to reduce any amount of left-over body portions that may hang or otherwise flap about.

Act 625 then includes securing the constrictive tension force on the object by inserting the first spike or the second spike (e.g., either of spikes 410A or 410B) through a hole provided on the additional portion of the elongated elastomeric body. In this manner, the tourniquet 400 in FIG. 4 is securely wrapped around appendage 405, and tourniquet 400 is able to continuously apply a constrictive tension force on appendage 405.

Accordingly, the disclosed embodiments generally relate to an improved tourniquet design and to a method of using that tourniquet. Through use of this tourniquet, any type of flow through an object may be restricted in a desired manner.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A tourniquet comprising:
   an elongated elastomeric body that includes a distal end and a proximal end, wherein the elongated elastomeric body is provided with a row of holes, each hole in the row being spaced a determined distance from one another, and wherein a first subset of at least three holes are proximate to the distal end and a second subset of at least three holes are proximate to the proximal end;

a buckle that is affixed proximately to the proximal end of the elongated elastomeric body; and a set of one or more protruding spikes that are affixed to the elongated elastomeric body and that are proximate to the buckle, wherein a loop is formed by the proximal end of the elongated elastomeric body passing through an opening of the buckle and wrapping backwards to extend parallel to a particular length of the elongated elastomeric body to thereby form said loop such that the loop passes through the buckle's opening, wherein each protruding spike in the set of one or more protruding spikes passes through the elongated elastomeric body at two separate locations, including at the proximal end and at the particular length of the elongated elastomeric body, such that the buckle is secured to the elongated elastomeric body via the loop, and wherein at least one protruding spike in the set of one or more protruding spikes passes through the elongated elastomeric body at least three times.

2. The tourniquet of claim 1, wherein the determined distance from one hole to another hole is between 0.75 inches and 4 inches.

3. The tourniquet of claim 2, wherein the determined distance is 1 inch.

4. The tourniquet of claim 1, wherein a length of the elongated elastomeric body is between 1 foot and 6 feet.

5. The tourniquet of claim 4, wherein the length is at least 3 feet.

6. The tourniquet of claim 1, wherein a width of the elongated elastomeric body is between 0.05 inches and 3 inches.

7. The tourniquet of claim 1, wherein a thickness of the elongated elastomeric body is between 0.05 inches and 0.25 inches.

8. The tourniquet of claim 1, wherein each spike in the set of one or more protruding spikes includes one or more ribbed portions.

9. The tourniquet of claim 1, wherein the buckle is a tri-glide buckle.

10. The tourniquet of claim 1, wherein the buckle is a type of buckle that provides a 2:1 mechanical advantage.

11. The tourniquet of claim 1, wherein the row of holes extends along a majority of a length of the elongated elastomeric body.

12. The tourniquet of claim 1, wherein a length of the elongated elastomeric body is at least 3 feet, a width of the elongated elastomeric body is at least 1 inch, and a thickness of the elongated elastomeric body is at least 0.05 inches.

13. The tourniquet of claim 1, wherein the set of one or more protruding spikes includes at least two spikes.

14. The tourniquet of claim 1, wherein at least one spike in the set of one or more protruding spikes has a length ranging between 0.25 inches and 1.5 inches.

15. The tourniquet of claim 1, wherein each spike in the set of one or more protruding spikes has a width that is a determined amount larger than a width of the holes in the row of holes.

16. A tourniquet comprising:
an elongated elastomeric body that includes a distal end and a proximal end, wherein the elongated elastomeric body is provided with a row of holes, each hole in the row being spaced a determined distance from one another;

a tri-glide buckle that is affixed proximately to the proximal end of the elongated elastomeric body; and a first spike and a second spike that are both affixed to the elongated elastomeric body and that are positioned proximately to the tri-glide buckle, wherein a loop is formed by the proximal end of the elongated elastomeric body passing through an opening of the tri-glide buckle and wrapping backwards to extend parallel to a particular length of the elongated elastomeric body to thereby form said loop such that the loop passes through the tri-glide buckle's opening, wherein the first spike passes through the elongated elastomeric body at two separate locations, including at the proximal end and at the particular length of the elongated elastomeric body, such that the tri-glide buckle is secured to the elongated elastomeric body via the loop, wherein the second spike passes through the elongated elastomeric body at two separate locations, including at the proximal end and at the particular length of the elongated elastomeric body, locations where the second spike passes through the elongated elastomeric body being different than locations where the first spike passes through the elongated elastomeric body, and wherein the first and second spike passes through the elongated elastomeric body at least three times.

17. The tourniquet of claim 16, wherein a length of the elongated elastomeric body is at least 3 feet, a width of the elongated elastomeric body is at least 1 inch, and a thickness of the elongated elastomeric body is at least 0.05 inches.

18. The tourniquet of claim 16, wherein the first spike includes a base that prevents the first spike from being able to be fully pushed through the elongated elastomeric body.

19. The tourniquet of claim 18, wherein the first spike includes multiple knurls.

* * * * *